United States Patent

Leichnitz

[11] Patent Number: 4,554,133
[45] Date of Patent: Nov. 19, 1985

[54] GAS MEASURING TESTING TUBE

[75] Inventor: Kurt Leichnitz, Gross Gronau, Fed. Rep. of Germany

[73] Assignee: Drägerwerk A.G., Fed. Rep. of Germany

[21] Appl. No.: 536,515

[22] Filed: Sep. 28, 1983

[30] Foreign Application Priority Data

Oct. 5, 1983 [DE] Fed. Rep. of Germany ....... 3236792

[51] Int. Cl.[4] ........................................... G01N 21/29
[52] U.S. Cl. ..................................... 422/87; 422/56; 422/57; 422/59; 422/86
[58] Field of Search .................................. 422/55–59, 422/84–87

[56] References Cited

U.S. PATENT DOCUMENTS 2,487,077 11/1949 Shepherd .............................. 422/59
3,399,973 9/1968 Grosskopf ............................. 422/86
3,420,205 1/1969 Morrison ............................... 422/56

FOREIGN PATENT DOCUMENTS 932750 9/1955 Fed. Rep. of Germany ........ 422/59
1037725 8/1958 Fed. Rep. of Germany ........ 422/57

Primary Examiner—Arnold Turk
Assistant Examiner—C. M. Delahunty
Attorney, Agent, or Firm—McGlew and Tuttle

[57] ABSTRACT

A highly sensitive test tube according to the invention increases the sensitivity of detection of a component in a gas substantially and thus enlarges the area of use of the test tube. It possesses a reagent strip impregnated according to the gas to be detected, which strip is held by a granular fill material between holding elements. The test gas, conveyed by a pump through the test tube, from which test gas the gas to be detected is removed at the reagent strip, is continually moved through the granular fill material and thoroughly mixed, so that the actual continually decreasing concentration of the gas component is available at the reagent strip. Upon complete removal of this gas component by reaction with the reagent strip, the concentration can then be read at the reagent strip. The narrow reagent strip, which takes up the entire gas component, evidences even small admixtures.

5 Claims, 2 Drawing Figures

GAS MEASURING TESTING TUBE

FIELD AND BACKGROUND OF THE INVENTION

This invention relates in general to gas testing devices and in particular to a new and useful highly sensitive test tube for determination of gas pollutants.

The advantage of the known test tube method with color indication resides in the possibility of measuring with relatively small test gas volumes (in general 0.5 to 2 liter) the gas pollution in the ppm range (1 ppm=1 cc/m$^3$). Quantitative measurements at concentrations less than ppm require special expenditures. Generally an increase of the test gas volume is involved. The advantage of the small test gas volume than no longer exists.

A gas dosimeter has become known which has a housing with a backwall and sidewalls. Toward the top it is open. It contains a colorimeter strip sensitive to the gas to be determined and to light. Optionally also a color standard may be arranged for comparison with the colorimeter strip (German No. AS 17 73 339).

A dosimeter tube made according to this design contains in a glass tube a paper strip provided with chemical reagents, which then react with the pollutant to be detected. A color change then occurs. In the state as supplied, the dosimeter tube is fused at both ends. For use it is opened by breaking off a tip at a weakened break line. The ambient air then penetrates into the interior of the tube by diffusion. With progressing diffusion and with the presence of the gas to be detected in the ambient air, the paper strip becomes discolored.

For use in a gas detector, in which a certain quantity of the gas (or air) to be tested is drawn by means of a sampling pump through the test tube for quantitative determination of the pollutant contained, this known dosimeter tube cannot be used. The test air would flow through the tube and hence past the reagent paper strip too fast. Continuous and hence quantitative discoloration of the reagent strip cannot occur because test air would react with the gas to be detected contained in it virtually simultaneously along the entire strip length and hence would discolor.

SUMMARY OF THE INVENTION

The invention provides a highly sensitive test tube for the quantitative determination of gas pollutions for use in known gas detectors with a gas sniffing pump preserving the advantages known from test tube methods such as the reliable test result known immediately on the site from directly carried specific test tubes.

According to the invention, a granular fill material holds a reagent strip impregnated according to the gas to be detected tightly against the inner surface of the glass tube between longitudinally spaced gas-permeable holding elements.

An advantage achieved with this invention is that because of the filling material the through flowing gas sample is in itself moved uninterruptedly and thereby mixed. The specific gas to be detected, which is removed from the test gas or test air at the reagent strip by reaction, will continuously be reduced in its concentration in the test gas. This becomes evident in the discoloration of the reagent strip and hence will indicate the concentration. By the summation of the percentual gas on only a small reagent surface already very low gas components become evident. The test tubes according to the invention, in which the granular fill material brings about the continuous mixing of the through flowing test gas, are therefore extremely sensitive.

The sub claims show further advantageous realizations of the subject of the invention. Accordingly, the reagent strip may be an impregnated paper strip or also an impregnated inert support material applied on the inner wall of the glass tube.

The granular fill material itself may also be impregnated especially separately, either to remove the gases which might disturb the reaction of the gas to be detected on the reagent strip, or else to transform the gas to be identified into a new measurable component, which then reacts on the reagent strip. These realizations underscore the simple and reliable possibilities of getting correct results with the sensitive test tube according to the invention.

Accordingly, it is an object of the invention to provide an improved testing device for testing for concentrations in a gas sample which comprises a testing tube for the flow of the gas sample therethrough which includes a granular fill material arranged between two gas permeable holders in the test tube and including a reagent strip which is pressed against the glass of the tube by a granular fill material.

A further object of the invention is to provide a testing tube which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figures 1, 2:
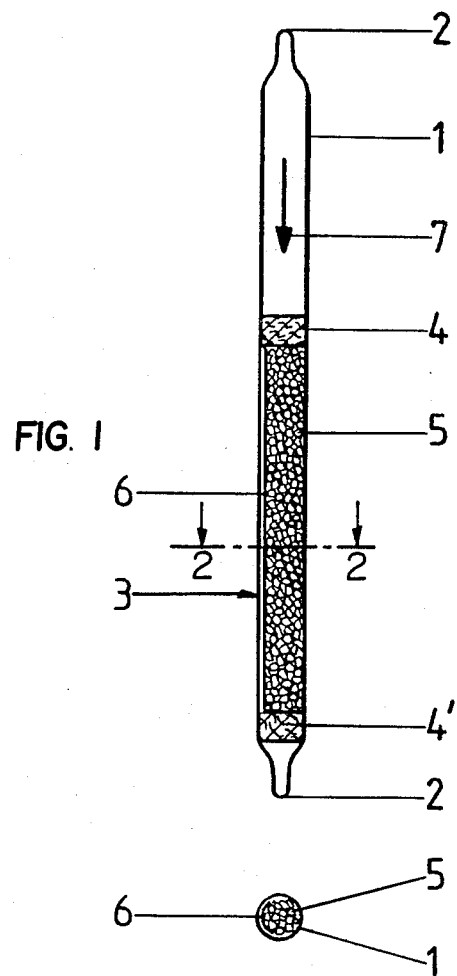
FIG. 1 is a longitudinal sectional view of a testing tube constructed in accordance with the invention.
FIG. 2 is a section taken along the line 2—2 of FIG. 1.

Referring to the drawings in particular the invention embodied therein comprises a test tube or testing tube 1 having breakable end portions or tips 2,2 in which contains a filling generally designated 3 arranged between transversely extending gas permeable holders 4 and 4'. The filling 3 comprises a reagent strip 6 which extends between the holders 4 and 4' and which is pressed against the glass of the tube 1 by a granular fill material 5.

A glass tube 1 with tips 2 adapted to be broken off contains a filling 3. The filling 3 is secured against vibration between gas permable holding elements 4. The filling 3 consists of a granular fill material 5 and a thin reagent strip 6. The reagent strip 6 is disposed on a part of the internal wall circumference between the holding elements 4. It is e.g. a reagent impregnated paper strip or a reagent impregnated inert support material which is applied on the inner wall of the glass tube. The direction of flow of the test gas is indicated by the arrow 7.

The granular fill material 5 may be impregnated with reagents in order to filter gases out of the test air, or also in order to transform the gas pollution to be determined into a new measurable component.

For the measurement the gas is drawn with a pump (not shown) through the test tube which is open after the tips 2 have been broken off. The gas pollution to be measured is moved uninterruptedly during flow through the granular fill material 5, hence is guided past the reagent strip 6 as a mixture and is there continually reacted quantitatively as it runs through in the flow direction, the reaction at the strip 6 being indicated by the color change.

While a specific embodiment of the invention has been shown and described in detail to illustrate the application of the principals of the invention, it will be understood that the invention may be embodied otherwise without departing from such principles.

What is claimed is:

1. An indicator tube for detecting gaseous contaminants in air comprising:
   a transparent indicator tube having an inner surface;
   two longitudinally spaced gas permeable holders positioned within said tube;
   granular fill material located within said tube between the gas permeable holders;
   a reagent impregnated strip extending between said gas permeable holders, said strip further being positioned between the granular fill material and a portion of the inner surface of said tube whereby the granular fill material holds said strip tightly against the portion of the inner surface of said tube.

2. An indicator tube according to claim 1, wherein said reagent impregnated strip is a reagent impregnated paper strip.

3. An indicator tube according to claim 1, wherein said reagent impregnated strip is a reagent impregnated inert carrier material applied to the inside of the indicator tube wall.

4. An indicator tube according to claim 1, wherein said granular fill material is impregnated with a catalyst with a reagent capable of effecting the chemical conversion an air contaminant not detectable by the reagent impregnated in said strip into a contaminant which is detectable by the reagent impregnated in said strip.

5. An indicator tube according to claim 1, wherein said granular fill material is impregnated with a catalyst with a reagent capable of effecting the removal from a gas containing a plurality of different detectable air contaminants those gases which may interfere with the reaction of a gas to be detected with the reagent impregnated in said strip.

* * * * *